| United States Patent [19] | [11] | 4,330,440 |
|---|---|---|
| Ayers et al. | [45] | *May 18, 1982 |

[54] ACTIVATED MATRIX AND METHOD OF ACTIVATION

[75] Inventors: John S. Ayers; Geoffrey S. Bethell; William S. Hancock, all of Palmerston North; Milton T. W. Hearn, Dunedin North, all of New Zealand

[73] Assignee: Development Finance Corporation of New Zealand, Wellington, New Zealand

[*] Notice: The portion of the term of this patent subsequent to Sep. 23, 1997, has been disclaimed.

[21] Appl. No.: 128,847

[22] Filed: Mar. 10, 1980

Related U.S. Application Data

[63] Continuation-in-part of Ser. No. 874,628, Feb. 2, 1978, Pat. No. 4,224,439.

[51] Int. Cl.³ ............................................. C08L 1/00
[52] U.S. Cl. ................................ 525/54.31; 65/30.1; 65/60.2; 65/60.3; 260/112 R; 260/112.5 R; 521/50; 525/375; 536/32; 536/43; 536/44; 536/48; 536/49; 536/50; 536/110; 536/51; 536/52; 536/115; 536/107; 536/108; 525/54.3; 525/281; 525/256; 525/257; 525/259; 523/209

[58] Field of Search ................... 65/30 R, 60; 536/32, 536/43, 44, 48, 49, 50, 110, 51, 52, 115, 107, 108; 260/6, 9, 112 R, 112.5 R; 521/50; 525/375

[56] References Cited

U.S. PATENT DOCUMENTS 4,211,865 7/1980 Ferruti et al. ...................... 536/107
4,224,439 9/1980 Ayers et al. ......................... 536/32

*Primary Examiner*—Melvyn I. Marquis
*Attorney, Agent, or Firm*—Holman & Stern

[57] ABSTRACT

The invention relates to the carbonylation of cross linked substituted and unsubstituted polysaccharides, their copolymers with macroporous synthetic polymers, macroporous synthetic polymers and rigid supports with pendant hydroxyalkyl groups. The carbonylated product can be used to prepare an affinity chromatography matrix which remains an uncharged species at varying pH's. The carbonylated product is also useful for the preparation of other compounds: Typical polysaccharides are agarose, starch, dextran, cellulose and regenerated cellulose, typical macroporous synthetic polymers are acrylamides, acrylates and methacrylates, typical rigid supports are silica beads coated with hydroxy alkyl groups and typical cabonylating agents are N,N'-carbonyl diimidazole; N,N'carbonyl di-1,2,3-benzotriazole; and N,N'-carbonyl di-1,2,4-triazole.

15 Claims, 5 Drawing Figures

ACTIVATED MATRIX AND METHOD OF ACTIVATION

CROSS REFERENCE TO RELATED APPLICATION

This is a continuation-in-part of our application Ser. No. 874,628 filed Feb. 2, 1978, entitled "Activated Matrix and Method of Activation" now U.S. Pat. No. 4,224,439.

BACKGROUND OF THE INVENTION

1. Field of the Invention

This invention relates to an activated matrix and to a method of activating the matrix. It further relates to the activated matrix further coupled to a ligand or leash and to a method of coupling the ligand or leash.

For the purposes of this specification, activating a matrix means carbonylating a matrix as defined in the appended claims with a suitable carbonylating agent. Activated matrix means a product of such a carbonylating reaction. Coupling a ligand or leash means substituting a ligand or leash having a good nucleophilic group, such as an amino group, into the carbonyl group of the activated matrix. A ligand is a substituent selected to be specifically attractive to a compound sought to be bound to the coupled matrix. Such binding may be by ion exchange or affinity chromatography, or for a radioimmuno assay, for hydrophobic chromatography or as an enzyme support or the like. A leash is a substituent which can be readily substituted into the carbonyl group of the activated matrix and then itself be substituted by a ligand. A macroporous synthetic polymer means a synthetic polymer which is sufficient porous to allow adsorbtion of macromolecules within the polymer. Coated glass beads refer to silica coated with a hydroxyl containing organic group such as an alkyl group by using a reactive silylating reagent which contains the necessary organic group (or precursor) attached to it by a stable Si-C bond. The hydroxyl groups on (or subsequently formed on) the organic group react with the carbonylating reagent to form an activated matrix.

The expression "a rigid support" is used in respect of a substance such as silica to which can be bonded directly an hydroxyl containing organic group as stated above.

2. Description of the Prior Art

Affinity chromatography is a separation technique exploiting the unique specificity of biological interaction to isolate naturally occurring compounds such as proteins, polysaccharides, glycoproteins and nucleic acids. Specific adsorptive properties are imparted to a bed material by covalently bonding an appropriate binding ligand to an insoluble matrix, i.e. by attachment of a suitable protein. The ligand acts to adsorb from solution a substance to be isolated, the isolated substance subsequently being dissolved by changing the experimental conditions after unbound substances have been washed away. The high specificities exploited by this method are natural specificities such as, for example, antigen/antibody, enzyme/inhibitor or hormone/carrier. Isolation of substances through this technique differs from conventional chromatography in which separation depends on gross physical and chemical differences between the substances.

Affinity chromatographic matrices are prepared by first activating a polysaccharide and then coupling a ligand and leash when required. In one such preparation agarose is reacted in a two-stage process as set out below. The first stage comprises treatment with cyanogen bromide to form an imido-carbonate compound of Formula I and the second stage comprises treatment with a primary amine to form an isourea compound of Formula II as set out hereinbelow:

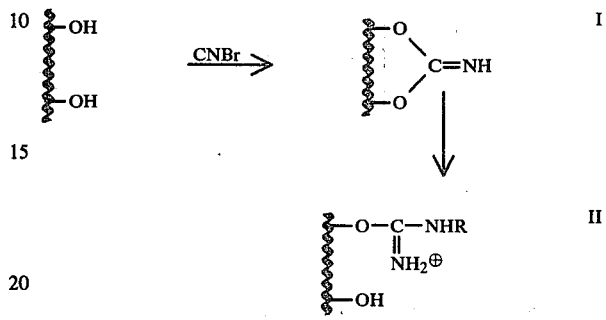

wherein R is a suitable affinity chromatography ligand. In the second stage reaction involving a nitrogen nucleophile the matrix becomes, in part, an ion exchange resin charged with the basic isourea group. This charge is present at pH 7 thus interfering with the specificity of the compound when attempting to isolate substances from biological materials. It also remains, but to a lesser extent, a higher pH levels. It will be appreciated that the specificity of the ligand would be considerably reduced by the presence of the charged groups thus reducing the desirability of the matrix activated by this method.

SUMMARY OF THE INVENTION

It has been found that a matrix activated according to the method forming one aspect of this invention exhibits an absence of charged groups such as are described above. Such an absence means that an activated matrix or a subsequently coupled matrix each has a much better specificity than matrices activated by the cyanogen bromide method.

It has also been found that a matrix activated according to one aspect of this invention has a higher concentration of activating groups than that obtained by activation by the cyanogen bromide method. This makes the activated matrix of this invention very attractive regardless of whether it is used directly or coupled with a ligand or leash.

The invention may be said broadly to consist in a compound of the general formula III:

wherein said MATRIX is a cross-linked water and organic solvent insoluble radical selected from the group consisting of:

cross-linked substituted and unsubstituted polysaccharides, copolymers of said polysaccharides with macroporous synthetic polymers, macroporous synthetic polymers and rigid supports with pendant hydroxyalkyl groups and Y is a member selected from the group consisting of imidazolyl; 1,2,4-triazolyl; or 1,2,3-benzotriazolyl.

In another aspect, the invention may be said broadly to consist in a method of preparing a compound of Formula III:

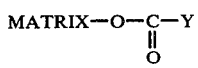   III wherein said MATRIX and Y are as defined above, which process comprises:

carbonylating said MATRIX in an organic solvent at a temperature of 0° C. to 80° C., the upper temperature limit being below the degradation temperature of MATRIX; with a carbonylating agent of the general formula IV—

   IV wherein Y is selected from the group of a dimidazolyl, a 1,2,4-triazolyl or a 1,2,3-benzotriazolyl.

In still a further embodiment the invention may be said broadly to consist in a compound of the general formula V:

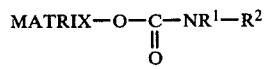   V wherein said MATRIX is as defined above, $R^1$ is selected from the group consisting of hydrogen, and an alkyl, and $R^2$ is selected from the group consisting of $-(CH_2)_n NH_2$, and $-(CH_2)_n CO_2H$, wherein n is an integer of from 2 and 12.

In a still further aspect the invention may be said broadly to consist in a process for the preparation of a compound of the general formula V as defined herein above: which process comprises reacting a compound of the formula III as defined above with an amine of the general formula $NHR^1R_2$ wherein $R^1$ and $R^2$ are as defined above.

Although the precise reaction mechanism of the activation process is not completely understood we believe any substrate or matrix having active hydroxy groups can be carbonylated by this method. Thus the choice of matrix is determined by the porosity required in use once it has been determined that active hydroxy groups are present.

BRIEF DESCRIPTION OF THE DRAWINGS

The invention may be more fully understood by having reference to the following drawings, wherein.

Figure 1:
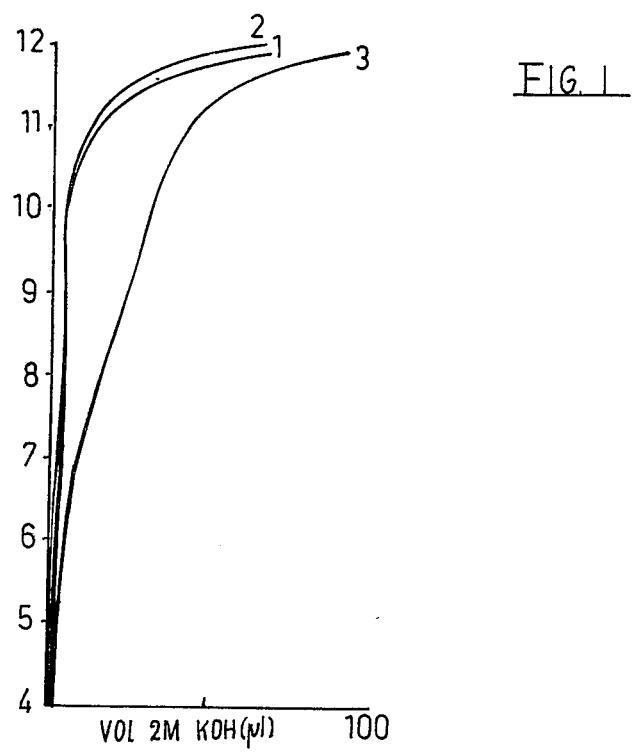
FIG. 1 shows titration curves of n-butylamine-SEPHAROSE in $H_2O$, curve 1 being SEPHAROSE CL-6B alone, curve 2 being n-butylamine-SEPHAROSE CL-6B coupled by the CDI method and curve 3 being n-butylamine-Sepharose CL-6B coupled by the cyanogen bromide method.

The figures will be referred to later during the discussion of the following examples.

EXAMPLES

1. ACTIVATION OF SEPHAROSE CL-6B MATRIX WITH CDI

SEPHAROSE CL-6B (a trade mark of Pharmacia Fine Chemicals for cross-linked agarose), 3 g Moist cake was washed sequentially with water, dioxan-water 3:7, dioxan-water 7:3 and dioxan (50 ml of each) and was suspended in dioxan (5 ml). 1,1-carbonyl diimidazole (CDI) (0.12 g) was added, and the suspension shaken at room temperature. It was washed with dioxan (100 ml) and used immediately. Duplicate experiments were carried out for times varying between 0.25 and 6 hr. and the products were analysed as described below.

2. ACTIVATION OF DIFFERENT MATRICES WITH CDI (a) Cross-linking Cellulose and Regenerated Cellulose WHATMAN CC-31 cellulose (a trade mark of W & R Balston Ltd.) (10 g) was reacted with 1 ml of epichlorohydrin in 30% NaOH solution at 65° C. for two hours. ENKA regenerated cellulose (10 g) was reacted in the same way.

(b) Hydropropylating Cross-linked Cellulose and Regenerated Cellulose

Cellulose and regenerated cellulose as in 2(a) were treated under identical conditions except that the reaction vessel was sealed, 0.2 ml and 1 ml of epichlorohydrin were used for the regenerated cellulose and cellulose respectively and 5 ml of propylene oxide was added in both cases.

(c) Activation

SEPHAROSE CL-6B and the products of Examples 2(a) and 2(b) were activated in a manner similar to that in Example 1. Reagents and yields are set out in Table 1.

TABLE 1

| | | Amount of Reaction | | | Yield | |
| | | | | | | % based on |
| MATRIX | Wt(g) | CDI (mmoles) | time (h) | Solvent | m moles | reagent |
| SEPHAROSE CL-6B | 3[1] | 0.93 | 0.25 | dioxan | 0.400 | 43 |

TABLE 1-continued

| MATRIX | Wt(g) | Amount of Reaction CDI (mmoles) | time (h) | Solvent | Yield m moles | % based on reagent |
|---|---|---|---|---|---|---|
| SEPHAROSE CL-6B | 3[1] | 2.07 | 2 | dioxan | 0.875 | 42 |
| Whatman Cellulose[3] | 0.2 | 0.93 | 0.5 | DMF[4] | 0.080 | 8.6 |
| Cellulose[3,5] | 0.2 | 0.93 | 0.5 | DMF[4] | 0.074 | 7.7 |
| Modified Cellulose[2,6] | 0.2 | 0.93 | 0.5 | DMF[4] | 0.436 | 47 |
| Modified cellulose[2,7] | 0.2 | 0.93 | 0.5 | DMF[4] | 0.636 | 69 |
| Modified regenerated cellulose[5,8] | 0.2 | 0.93 | 0.5 | DMF[4] | 0.644 | 69 |

[1]Weight of moist cake,
[2]Methanol dried
[3]Whatman microgranular cellulose CC-31
[4]Presoaked overnight,
[5]Freeze dried
[6]Cellulose CC-31 (10g) after reaction with epichlorhydrin (1ml) in 30% NaOH
[7]Same product as 6 except that 5ml of propylene oxide was also added
[8]Derived from ENKA regenerated cellulose (10g) with 0.2ml of epichlorhydrin, 5ml propylene oxide in 30% NaOH.

Figure 4:
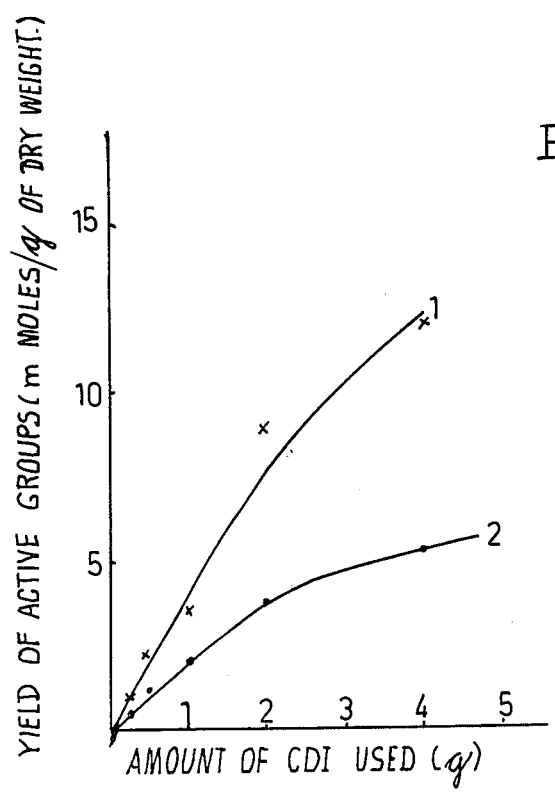
FIG. 4 shows comparative plots of yields of active groups with varying matrices. Curve 1 is the yield when cross-linked hydroxypropylated regenerated cellulose is the matrix and the curve 2 is the yield for cross-linked agarose.

It will also be seen from FIG. 4 that the yield of hydroxypropylated cross-linked regenerated cellulose is greater than that of SEPHAROSE CL-6B when each is activated with CDI.

3. COUPLING OF LIGANDS OR LEASHES TO ACTIVATED MATRIX (a) The material from example 1 was treated at 4° C. overnight with n-butylamine (1.4 g), in water (9 ml) at pH 10 and was washed sequentially with water (200 ml) 1 M NaCl (100 ml) and water (200 ml). Materials for titration were further washed with 0.005 M HCl (200 ml).

(b) The coupling as described in example 3(a) was repeated using 1,6 diaminohexane. Materials for titration were as before.

(c) Similarly an activated matrix from example 1 was coupled with 6-amino hexanoic acid.

(d) Coupling of ethanolamine to 6-aminohexanoic acid SEPHAROSE

The coupled SEPHAROSE CL-6B from example 3(c) (3 g moist cake) was treated with ethanolamine (0.5 g) and 1-cyclohexyl-3-(2-morpholinoethyl)-metho-p-toluene suphonate (CMC) (0.5 g) at pH 6 overnight at room temperature. The material was washed as for the coupling step.

(e) Cross-linked agarose (3 g moist cake) CDI (333 mg), 2 hour activation gave 875 μmoles of active groups (by titration), coupled with 1.4 g of 6-aminohexanoic acid at pH 10 (left 12h) and gave 390 μmoles of titratible carboxyl groups (pk 4.7). This gave a capacity of 1.95 mmoles/g of dry weight.

4. ANALYSIS OF ACTIVATED MATRIX

The activated matrices (0.2 g) from example 1 and 2(c) were hydrolysed overnight at room temperature in 0.15 M NaOH (50 ml). 20 ml portions of the supernatant liquid were then titrated under nitrogen for carbonate in the presence of hydroxide ions. The solutions were retitrated over the same pH range, after all the carbon dioxide had been expelled by flushing with nitrogen at pH 2.5. The second figure gave the imidazolyl content of the sample. The difference between the two figures gave the carbonate content of the sample.

A sample of the same activated matrix was found to have 6.92 and 6.99% nitrogen by elemental analysis. Calculated on the basis of the above titration figure the expected value for N was 6.48%.

Coupled matrices (0.2 g dry weight) from examples 3a to 3e were titrated potentiometrically under nitrogen using 2 M KOH 1 μl aliquots) under nitrogen from pH 3–11.7 in a total of 8 ml H$_2$O. Titrations were performed using a Radiometer TTT2 automatic titration assembly.

5. COMPARISON WITH CNBr ACTIVATED SEPHAROSE

In order to compare the linkage in an affinity matrix from CDI activated SEPHAROSE with that from cyanogen bromide activated SEPHAROSE, (prepared by the method described in Analytical Biochemistry 60, 149–152 (1974)), n-butylamine was coupled to each activated SEPHAROSE.

The titration curves for the two coupled activated matrices as well as the control with unactivated SEPHAROSE alone are shown in FIG. 1. It will be seen that the titration curve of n-butylamine-SEPHAROSE (CDI method) was virtually identical to that of the untreated SEPHAROSE. That of n-butylamine-SEPHAROSE (cyanogen bromide method) clearly indicated the presence of charged groups (pK$_a$8, 240 μmoles per dry g) usually considered to be isoureas.

Figure 2:
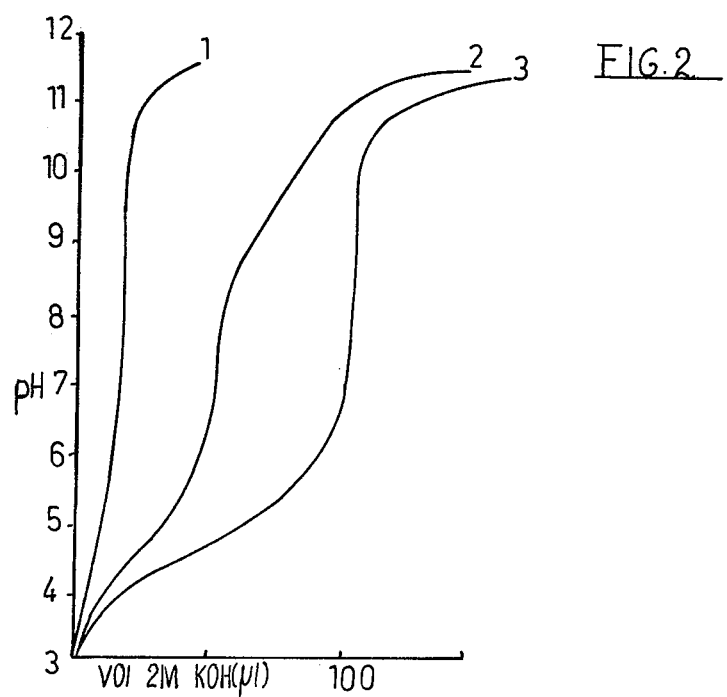
FIG. 2 shows titration curves of 6-amino hexanoic acid SEPHAROSE in 0.5 M NaCl. Curve 1 is 6-amino hexanoic acid-SEPHAROSE CL-6B coupled by the CDI method (103 micromoles-g), curve 2 is 6-amino hexanoic acid-SEPHAROSE CL-6B coupled by the cyanogen bromide method and plot 3 being 6-amino hexanoic acid-SEPHAROSE CL-6B coupled by the CDI method (825 micromoles-g).
Figure 3:
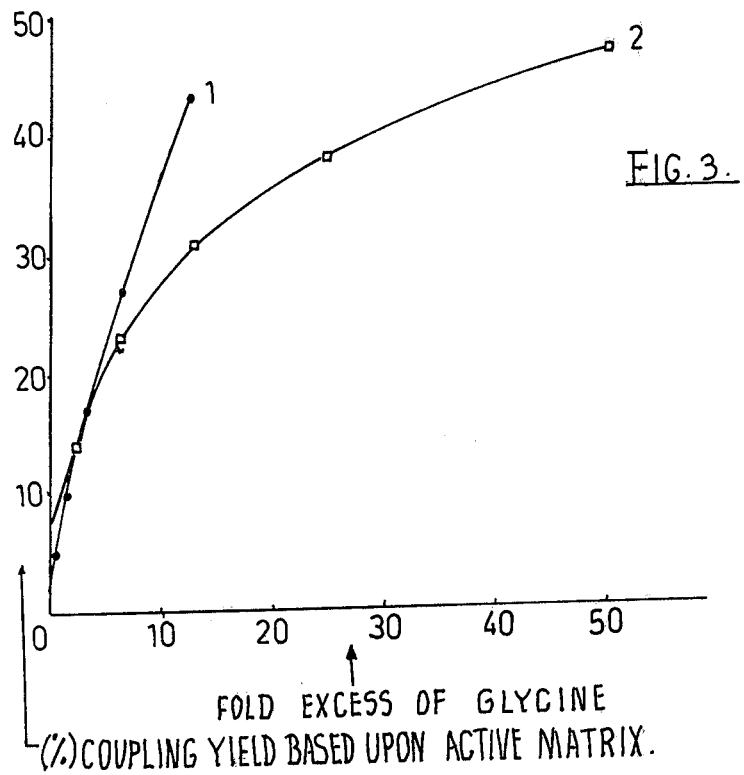
FIG. 3 shows comparative plots of coupling yields of glycine. Curve 1 is a CDI activated matrix while curve 2 is a CNBr activated matrix.

6-Aminohexanoic acid-SEPHAROSES were then prepared by each method and examined by titration to show that amines did indeed couple by this new method. The titration curves comparing these two products are shown in FIG. 2. The titration curves indicated the presence of carboxyl groups (pk$_a$4.7, 103 and 825 μmoles per dry g) but the curve was identical to that of untreated SEPHAROSE CL-6B at alkaline pH's. On the other hand the titration curve of 6-aminohexanoic acid-SEPHAROSE (cyanogen bromide method) indicated the presence of two charged groups (pk$_a$ 4.7, carboxyl, 390 μmoles per dry g, and pk$_a$ 9.5, isourea) in an approximate ratio of 1.2:1.0. This is close to the expected value of 1:1 if an isourea group is formed on attachment of each molecule of the acid.

The 6-aminohexanoic acid-SEPHAROSE (CDI method) was then blocked with ethanolamine by means of a water soluble carbodiimide and a further titration curve was run. This indicated an absence of charged groups in the pH range 3–10 demonstrating that a leash and a ligand can be attached by this method without introducing additional charged groups or leaving unblocked carboxyl functions.

These experiments show that no charged groups are introduced on to SEPHAROSE CL-6B by activation with 1,1'-carbonyl diimidazole and subsequent treatment with simple amines.

6. ACTIVATION OF CROSS-LINKED ALLYL DEXTRAN

Cross-linked allyl dextran in bead form (obtained from Pharmacia Fine Chemicals under the trade name of Sephacryl S-300) was collected on a sintered-glass filter from an aqueous suspension of the beads. A sample of the wet beads equivalent to 0.2 g dry weight was solvent exchanged into dioxan by washing it sequentially with water, dioxan-water 3:7, dioxan-water 7:3, and dioxan. The beads were then suspended in 5 ml of dioxane and reacted with carbonyl diimidazole (CDI) by mixing the suspension and CDI for 30 minutes at room temperature. The activated allyl dextran beads were collected on a filter, washed with dioxan (100 ml) and analysed for active groups.

7. ANALYSIS OF ACTIVATED MATRIX

The active groups on the allyl dextran beads from example 6 were hydrolysed in 30 minutes in 0.5 M NaOH (50 ml) at room temperature. Portions of the supernatant liquid (20 ml) were then titrated under nitrogen for carbonate in the presence of hydroxide ions. The solution was retitrated over the same pH range after all the carbon dioxide had been expelled by flushing with nitrogen at pH 2.5. The second titration figure gave the imidazole content of the sample.

8. ACTIVATION OF OTHER MATRICES WITH CDI

Other matrices were activated with CDI in a manner similar to that in example 6 using either dioxan or dimethylformamide (DMF) as the solvent. Matrices supplied in the dry form were swelled in water before solvent exchange but the same or greater yields of active groups were obtained by preswelling the matrices directly in DMF for 16 hours and then adding the CDI. The active groups were determined as in example 7 except for coated glass beads which are unstable at pH's greater than 8. In this case the active imidazole groups were hydrolysed at pH 3 for four hours. The pH was maintained at 3 by the automatic addition of the acid during this period. Other details of the reactions and the levels of activation obtained are set out in Table 2.

TABLE 2

| MATRIX[1] | SOL-VENT | Yield of Active Groups (m mol./gl) CDI used (g./0.2 g.matrix) | | |
|---|---|---|---|---|
| | | 0.075 | 0.15 | 0.30 |
| Cross-linked agarose[2] | Dioxan | 0.8 | 1.5 | 2.4 |
| Microgranular cellulose[3] | (Dioxan | 0.4 | 0.5 | 0.7 |
| | (DMF | 0.3 | 0.4 | 0.7 |
| Cross-linked dextran[4] | DMF | 0.8 | 1.9 | 2.8 |
| Cellulose beads[5] | Dioxan | 0.8 | 1.3 | 1.9 |
| Cross-linked allyl dextran[6] | Dioxan | 0.5 | 1.1 | 1.9 |
| HP-Reg.Cellulose[7] | (Dioxan | 1.0 | 1.6 | 2.8 |
| | (DMF | 0.8 | 1.2 | 2.5 |
| Agarose-polyacrylamide[8] (copolymer) | Dioxan | 0.6 | 0.9 | 1.2 |
| Coated glass beads[9] | Dioxan | 0.3 | 0.35 | — |
| Hydroxyethyl Methacrylate[10] | (Dioxan | 1.3 | 1.9 | 2.5 |

TABLE 2-continued

| MATRIX[1] | SOL-VENT | Yield of Active Groups (m mol./gl) CDI used (g./0.2 g.matrix) | | |
|---|---|---|---|---|
| | | 0.075 | 0.15 | 0.30 |
| (polymeric gel) | (DMF | 0.3 | 0.7 | 1.2 |

[1]Dry matrices (0.2 g) were preswelled in water before solvent exchange.
[2]"Sepharose CL-6B" from Pharmacia Fine Chemicals.
[3]"Whatman CC-31" from Whatman Ltd.
[4]"Sephadex G-25" from Pharmacia Fine Chemicals.
[5]Cellulose regenerated in bead form from cellulose acetate from G. Tsao, Purdue University.
[6]"Sephacryl S-300" from Pharmacia Fine Chemicals.
[7]Hydroxypropylated regenerated cellulose derived from ground regenerated cellulose (10g) by reaction with epichlorohydrin (0.8 ml) and propylene oxide (5 ml) in 30% NaOH.
[8]"Ultrogel AcA 44" from LKB.
[9]"Glycophase G" from Pierce Chemical Company, glass beads coated with dihydroxypropyl groups.
[10]"Spheron" P100 from Koch light, U.K.

9. COUPLING OF 6-AMINOHEXANOIC ACID TO ACTIVATED MATRICES

The activated matrices prepared from 0.2 g dry weight of matrix as set out in example 8 were each washed on a filter with dioxan or DMF and then drained of excess solvent. Each one was added to 8 ml of 1 M sodium carbonate (pH 10) containing 5.4 m mol of 6-aminohexanoic acid and mixed overnight at room temperature.

The coupled matrix was washed successively with water, 1 M NaCl, water, 0.01 M hydrochloric acid and deionized water. The 6-aminohexanoic acid coupled matrix in its acid form was titrated in 1 M NaCl to pH 7.5 with standard sodium hydroxide.

The number of coupled groups and efficiency of coupling are set out in Table 3.

TABLE 3

| Matrix | Solvent | Active groups (m mol./g.) | Coupled Groups (m mol./g.) | Coupling Efficiency % |
|---|---|---|---|---|
| Cross-linked agarose | Dioxan | 2.4 | 0.84 | 35 |
| Microgranular cellulose | " | 0.7 | 0.21 | 30 |
| Cross-linked dextran | DMF | 2.8 | 0.75 | 27 |
| Cellulose beads | Dioxan | 1.9 | 0.48 | 25 |
| Cross-linked allyl dextran | Dioxan | 1.9 | 0.99 | 52 |
| HP-Regenerated cellulose | DMF | 2.5 | 1.11 | 44 |
| Agarose-polyacrylamide (copolymer) | Dioxan | 1.2 | 0.45 | 38 |
| Hydroxyethyl methacrylate (polymer) | Dioxan | 1.87 | 0.3 | 16 |

Figure 5:
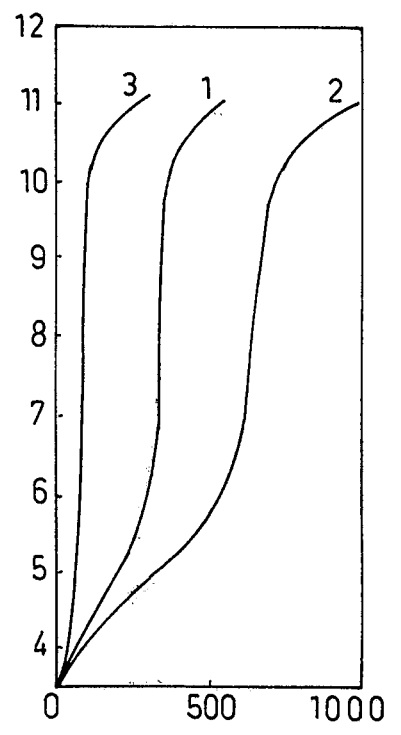
FIG. 5 shows the titration curves for 6-aminohexanoic acid coupled to the activated matrices by the carbonyldiimidazole method. Curve 1 is 6-aminohexanoic acid coupled to agarose-polyacrylamide copolymer, curve 2 is 6-aminohexanoic acid coupled to cross-linked allyl dextran, curve 3 is that obtained for both matrices before activation.

Titration curves (FIG. 5) for the activated matrices coupled with 6-aminohexanoic acid were produced by titrating the coupled matrices under nitrogen with 0.2 M sodium hydroxide (10 μl aliquots) from acid solution in 1 M sodium chloride. After the addition of each aliquot of sodium hydroxide the matrix was allowed two to five minutes to come to complete equilibrium before the pH was recorded each time.

The synthetic macroporous matrix "Spheron" also showed a complete absence of charged groups between pH 7 and 10 after activation and coupling with CDI and 6-aminohexanoic acid.

10. COUPLING OF GLYCYLGLYCINE TO ACTIVATED GLASS BEADS

Coated glass beads, "Glycophase G" from Pierce Chemical Company, (6 g) were activated with CDI (3 g) in dioxan (40 m) as described in example 8. Glycylglycine (2.8 g) was dissolved in water (40 ml) and adjusted to pH 8. The activated glass beads were added to the solution of glycylglycine and lightly shaken for 3 days at room temperature. At the end of this time the pH was shifted to 3.5 and the beads left for 4 hours at this pH to remove any unreacted imidazolyl groups. The beads were washed with water, 1 M sodium chloride and finally water again.

A small sample of the coupled coated glass beads were taken and washed with excess 0.005 M hydrochloric acid and then deionized water. Titration of the glycylglycine beads with 0.2 M sodium hydroxide showed that they had 0.103 moles- $CO_2H$ groups per gram dry weight.

11. COMPARISON OF ACTIVATING REAGENTS

The following activation reagents were tried:

(a) N,N' carbonyl diimidazole (CDI) in dioxan
(b) N,N' carbonyl di-1,2,4-triazole (CDT) in dioxan
(c) N,N' carbonyl di-1,2,3-benzotriazole (CDB) in dioxan
(d) Cyanogen bromide in 1 M sodium carbonate followed by hydrolysis in 1 M HCl for 0.5 h (CNBr/HCl)
(e) Cyanogen bromide in 1 M sodium carbonate for comparison purposes (CNBr).

The following results (table 4) were obtained on a 3 g moist cake of SEPHAROSE in 5–6 ml dioxan or 12 ml 1 M sodium carbonate as appropriate.

TABLE 4

| Method | Reaction Time | Mmoles reagent Used | Activation Yield (μmoles/sample) | % Yield based on reagent |
|---|---|---|---|---|
| CDI | 15 min | 0.93 | 400 | 43 |
| CDT | 15 min | 0.93 | 315 | 35 |
| CDB | 7 days | 0.63 | 80 | 12.7 |
| CNBr | 4 min | ~6 | 105 | 2 |
| CNBr/HCl | 4 min plus 30 min | ~6 | 105 | 2 |

For the first three reagents, activation yeilds were obtained by hydrolysing the dioxan washed product in 0.15 M alkali overnight at room temperature and then titrating the supernatent liquid for carbonate ions. Yields for the CNBr reagent were based on the Kjeldahl nitrogen determination thus:

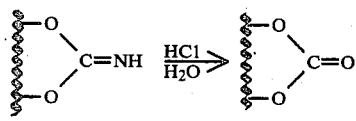

Hence the difference in nitrogen content on the matrix before and after hydrolysis with 1 M HCl gave the number of active imidocarbonate groups formed. This figure also gave the number of active cyclic carbonate groups produced by this hydrolysis. A sample of the acid hydrolysed product was also analysed by the carbonate titration method above and gave a figure of 150 μmoles/sample. This is higher than the Kjeldahl figure, not surprisingly, since the slow reaction:

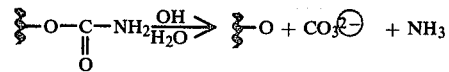

also takes place and therefore some of the inactive carbamate groups are also "counted".

The reactions between SEPHAROSE and CDI and CDT could be left until it was convenient to do the work up, activation yields being identical for reaction times of between 0.25 and 6 hours. This is in direct contrast to the CNBr method which requires the work up to be done as quickly as possible. In addition, the activation yield could be greatly increased if more CDI were used whereas the CNBr method, only a further 10% of active group groups were present even if the amount of reagent was quadrupled.

CDB was used to activate SEPHAROSE but the reaction was very slow. Even after 7 days, yields were only 80 μmoles and only 13% of the reagent had been consumed. This was probably due to a steric effect. As in the case of CDI, the active species was found to be acyclic. Benzotriazole was found by titration analysis.

Cyclic carbonates were formed on SEPHAROSE by the known procedure of hydrolysing in acid solution an imidocarbonate formed by the CNBr method. Treatment of the imidocarbonate with 1 M HCl for 0.5 h gave a product which averaged 105 μmoles of groups per 3 g of wet resin. A similar hydrolysis with 0.001 M acid gave 92 μmoles of cyclic carbonates. 1 M acid was generally used as it was found not to significantly degrade the matrix, even during 0.5 h reaction times.

12. DETERMINATION OF COUPLING TIMES

The activated matrices above were subjected to hydrolysis at various pH's. These reactions were monitored by measuring the amount of alkali (or acid in the case of pH 5) required to maintain the required pH as a function of time. The reactions were found not to be first order in that successive half-lives tended to increase. Table 5 shows the total times for each reaction carried out at room temperature.

TABLE 5

| Activation Method | Reaction time (hrs) | | | |
|---|---|---|---|---|
| | pH 5 | pH 8½–9 | pH 10 | pH 11 |
| CDI | 20 | 30 | 10 | 1.5 |
| CDT | — | 4 | 1.5 | — |
| CDB | — | 1 | 1 | — |

These figures give a measure of the length of time for which any coupling reaction should be left in order to completely remove all active groups. As a result of this, reactions with the CDI activated matrix were generally left overnight at pH 10 and over the weekend at pH 9, or treated with an excess of ethanolamine to block unreacted active groups. The greater stability of the CDI relative to the CNBr activated matrix simplifies its filtration and washing before addition of the ligand or leash.

The CDT activated matrix was much more reactive than the CDI matrix and could be used where rapid coupling reactions are required.

13. COMPARISON OF COUPLING YIELDS

A series of couplings of three amines of differing pK values were carried out to find out the comparative reactivities towards amines and water of the active groups on each matrix. The amines selected were 6-aminohexanoic acid (pKa~11), glycine (pKa 9.8) and glycylglycine (pKa 8.1). In addition 1,6-diaminohexane (pKa~11) was tried in one case. The amines were present in large excess (5.4 mmoles) and were maintained at the required pH either by pH statting or by buffering using 1 M carbonate at pH 10 or 1 M N,N,N',N'-tetramethylethylene diamine at pH 9. At pH 11 6-aminohexanoic acid was used without additional buffer. The results are tabulated in Table 6.

(b) Soybean trypsin inhibitor as ligand (CDI method). Sepharose CL-6B (1 g moist cake) was activated with CDI (0.15 g) and divided into two equal portions. Each was treated with soybean trypsin inhibitor (15 mg) in 1 ml buffer for two days at 4° C. Portion (i) was 1 M in sodium carbonate at pH 10. Portion (ii) was 1 M in N,N,N',N'-tetramethylethylene diamine at pH 9. The materials were washed alternately five times with 0.1 M sodium bicarbonate and 0.1 M sodium acetate (pH4) each containing 0.5 M salt.

(c) Soybean trypsin inhibitor attached via a leash (CDI method) 6-aminohexanoic acid-SEPHAROSE CL-6B was prepared as in example 9a (half scale) and was treated at room temperature for 24 hours at pH 4.7 with STI (15 mg) and CMC (0.12 g). The material was washed as in example 9b.

TABLE 6

| Method | Active groups (μmoles/sample) | 6-aminohexanoic Acid PH 9 | 6-aminohexanoic Acid PH 10 | 6-aminohexanoic Acid PH 11 | 1,6-diaminohexane PH 10 | 1,6-diaminohexane PH Dioxan Solution | Glycine PH 9 | Glycine PH 10 | Glycylglycine PH 9 | Glycylglycine PH 10 |
|---|---|---|---|---|---|---|---|---|---|---|
| CDI | 400* | 64 | 130 | 162 | 130 | 280 | 122 | 194 | 224 | 80 |
| CDT | 315 | 86 | 155 | — | — | — | 149 | 198 | 154 | 70 |
| CBD | 70 | — | 43 | — | — | — | — | — | — | — |
| CNBr | 105 | 64 | 65 | — | — | — | 49 | 50 | 34 | 30 |
| CNBr/HCl | 105 | 31 | 44 | — | — | — | 30 | 39 | 30 | 14 |

*Washed with water prior to reaction

The figures were obtained by titrations of the end groups on the matrix with standard alkali.

For a given amine under the same conditions, the percentage coupling yields of each activated matrix are very similar. For example, generally for 6-aminohexanoic acid at pH 10 each activated matrix has 45–60% of its active groups available for coupling. Each amine appears to couple best at a pH which is about 1 unit above its pKa value. This is the point at which an increase in pH will not increase the free amine concentration but will increase the concentration of hydroxide ions and hence the hydrolysis rate. Conversely a decrease in pH, whilst it will decrease the hydroxide ion concentration, will also decrease the concentration of the free amine, more of it existing as the protonated form.

Summarising therefore, on the grounds of cost and capacity the CDT and CDB activated matrices would not appear to offer any advantage over the cheaper CDI method except that the CDT method would seem to be comparable with the standard CNBr method with the added advantage of being more pleasant to handle.

There is little doubt however that the greatest advantage of the methods based on the carbonyl reagents over the CNBr method lies in the fact that no charged groups are introduced on to the matrix during the coupling step.

14. USE OF ACTIVATED MATRIX AS TRYPSIN AFFINITY SUPPORT

Preparation of trypsin affinity supports (a) The activated SEPHAROSE Cl-6B (from 3 g moist cake and 50 mg CDI) was treated overnight at 4° C. with 6-aminohexanoic acid (0.7 g) in H$_2$O (9 ml) at pH 10. It was then washed as in Example 3a. Two 1 ml portions of this material were treated at pH 4.7 for 24 hours at room temperature with CMC (0.12 g) and p-aminobenzamidine hydrochloride (5 or 10 mg) and subjected to the same washing procedure.

(d) Soybean trypsin inhibitor as ligand (CNBr method). SEPHAROSE Cl-6B (1 g moist cake) was activated with cyanogen bromide. The material was divided into two equal portions and then treated with STI as in example 9b. Affinity chromatography was carried out on 0.4–1 ml samples packed into Pasteur pipettes. The equilibrating, loading and washing buffer was 0.05 M Tris (pH8) and desorbtion was carried out with 3 mM HCl. All solutions contained 0.5 M NaCl. Loadings were 20 mg trypsin in 16 ml buffer for examples 9a, 9b and 9d and 10 mg in 8 ml for example 9c.

Trypsin was analysed directly by u.v. spectroscopy at 280 nm.

The affinity supports described above had the trypsin capacities indicated in Table 7. In control experiments, 6-aminohexanoic acid-SEPHAROSE (both CDI and cyanogen bromide methods) shows no affinity for trypsin. In all cases removal of unbound trypsin was complete (u.v. monitor at 280 nm) and the subsequent pH shift caused rapid elution of the bound trypsin.

The CDI-activated affinity columns all had high capacities for trypsin, well up to the standards required for good preparative procedure. The capacities of columns III and V where STI was coupled directly to the CDI-activated matrix were somewhat lower than those of the corresponding columns IV and VI made by the cyanogen bromide method. However the lack of charged isourea groups introduced at the coupling stage with the new procedure is probably the most significant difference from the cyanogen bromide method. In fact the higher binding capacity of the cyanogen bromide product could be at least partly due to non-specific binding.

The trypsin capacities of columns I and II, table 7, i.e. those on which the ligand was coupled to a 6-aminohexanoic acid spacer group, were equally impressive.

In addition CDI activation of polysaccharide matrices offers a method of insolubilising a variety of organic molecules which contain amino groups. Such products are of value in the preparation of insolubilised receptors for radio immuno assays, insolubilised enzymes and ion exchange groups linked directly or through leashes.

TABLE 7
CAPACITIES OF TRYPSIN AFFINITY SUPPORTS

| AFFINITY COLUMN | TRYPSIN CAPACITY OF COLUMN (examples 14a–14d)[1] | |
|---|---|---|
| | Per ml | Per sample |
| I p-aminobenzamidine-SEPHAROSE, CDI method | 12.4, 12.4[1] | 12.2, 13.0[1] |
| II trypsin inhibitor-6-aminohexanoic acid leash-SEPHAROSE, CDI method | 3.6 | 6.4 |
| III trypsin inhibitor-SEPHAROSE, CDI method, pH 9 coupling | 2.4 | 1.0 |
| IV trypsin inhibitor-SEPHAROSE, CNBr method, pH 9 coupling | 3.8 | 2.62 |
| V trypsin inhibitor-SEPHAROSE, CDI method, pH 10 coupling | 5.5 | 2.10 |
| VI trypsin inhibitor-SEPHAROSE, CNBr method, pH 10 coupling | 8.9 | 6.42 |

[1]The two values were for 5 or 10 mg of p-aminobenzamidine respectively.

15. USE OF ACTIVATED MATRIX TO IMMOBILISE BIOLOGICALLY ACTIVE COMPOUNDS

The examples described in Table 8 were chosen to demonstrate that biologically active molecules could be linked to a polysaccharide matrix by the CDI method under conditions which allowed retention of their activity (for example see (b), (c) and (g) in Table (8). Other examples should provide useful materials for radioimmunoassays and radio-receptor assays (see example (a), (f) and (g) in table (8).

TABLE 8
SOME FURTHER EXAMPLES OF ORGANIC MOLECULES WITH AMINO GROUPS LINKED TO SEPHAROSE CL-6B WITH CDI[1]

| PROTEIN | COUPLING YIELD (%) | PROTEIN CONCENTRATION ON THE INSOLUBILISED SUPPORT ($\mu$moles/g) |
|---|---|---|
| (a) sulphanilic acid-azo-bovalbumin | 90[2] | 1.5[3] |
| (b) human thyroglobulin[5] | 94[2] | 0.6[3] |
| (c) bovine thyroid stimulating hormone (TSH)[6] | 88[2] | 3.6[3] |
| (d) porcine insulin | 100[2] | 4.5[3] |
| (e) human immunoglubulin | 87[2] | 1.5[3] |
| (f) creatinine | — | 18[4] |
| (g) 3,3',5-thyronine[7] | 78[2] | 52[4] |

[1]Prepared using the same method as for soybean trypsin inhibitor, each sample was coupled to 2g of CDI-activated SEPHAROSE (moist cake weight) which had been reacted with 50 mg of CDI at pH 8.5 (0.1M borate).
[2]Estimated by the decrease in optical density (at λmax of the sample) of the washings relative to the coupling reaction.
[3]Determined by amino acid analysis of a 0.6g sample which had been hydrolyzed with 6N HCl, 110°, 24h.
[4]Determined by N elemental analysis.
[5]Binds significant quantities of human thyroglubulin autoantibodies, in fact the binding capacity is identical to the corresponding CNBr activated matrix.
[6]Binds rabbit antibovine TSH antibodies, and 1 ml of gel neutralised completely at 1:32 dilution of a standard antibody preparation.
[7]1 ml of gel completely neutralised 1:100 dilution of a rabbit antithyronine antibody.

16. USE OF ACTIVATED ULTROGEL ACA 44 and SEPHAROSE CL6B TO IMMOBILISE BIOLOGICALLY ACTIVE COMPOUNDS The following proteins: (1) human thyroglobulin (h-Tg), (2) human immunoglobulin G(h-IgG), (3) bovine thyrotrophin (b-TSH), (4) sheep thyroid plasma membrane binding protein (S-TS aab BP), were each bound to their respective affinity supports in the manner described in relation to example 14. The affinity supports were activated in the manner described in example 8. The matrix bound proteins were estimated on the basis of recovered proteins. The coupling yields and bioadsorbent capacities are set out in Table 9.

TABLE 9
EXAMPLES OF PROTEINS COUPLED TO CDI ACTIVATED ULTROGEL ACA 44 AND SEPHAROSE CL6B

| | CL-6B | | ULTROGEL ACA 44 | |
|---|---|---|---|---|
| PROTEIN | Coupling yield % | Bioadsorbent Capacity $\mu$moles/g | Coupling Yield % | Bioadsorbent Capacity $\mu$moles/g |
| h-Tg | 62 | 0.02 | 41 | 0.01 |
| h-IgG | 92 | 0.12 | 62 | 0.08 |
| b-TSH | 80 | 0.14 | 69 | 0.12 |
| s-TSaab-BP | 91 | 0.21 | 52 | 0.12 |

What we claim is:

1. A compound of the general formula III

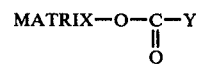

wherein MATRIX is a water and organic insoluble radical selected from the group consisting of:
cross-linked polysaccharides, subsituted by $C_2$–$C_8$ alkyl or alkenyl groups, macroporous synthetic polymers, co-polymers of cross-linked substituted polysaccharides with macroporous synthetic polymers, cross-linked co-polymers of unsubstituted polysaccharides with macroporous synthetic polymers, and rigid supports with pendant hydroxyalkyl groups, and Y is a member selected from the group consisting of:
imidazolyl; 1,2,4-triazolyl; and 1,2,3-benzotriazolyl.

2. A compound as claimed in claim 1 wherein said MATRIX is a polysaccharide selected from the group consisting of agarose, starch, dextran, cellulose, regenerated cellulose, hydroxy $C_2$–$C_4$ alkylated cellulose and hydroxy $C_2$–$C_4$ alkylated regenerated cellulose.

3. A compound as claimed in claim 2 wherein said MATRIX is cross-linked allyl dextran and Y is imidazolyl.

4. The compound as claimed in claim 1 wherein said MATRIX is a copolymer of polyacrylamide with a cross-linked substituted or unsubstituted polysaccharide selected from the group consisting of: agarose, starch, dextran, cellulose, regenerated cellulose, hydroxy $C_2$–$C_4$ alkylated cellulose and hydroxy $C_2$–$C_4$ alkylated regenerated cellulose.

5. The compound of claim 4 wherein said MATRIX is an agarose/polyacrylamide copolymer and Y is imidazolyl.

6. The compound of claim 1 wherein said MATRIX is a said rigid support comprising silica beads having pendant $$-CH_2CH-CH_2O-$$
$$\phantom{-CH_2CH-}|$$
$$\phantom{-CH_2CH}OH$$

radicals and Y is imidazolyl.

7. The compound of claim 1 wherein said MATRIX is hydroxyethyl methacrylate and Y is imidazolyl.

8. A process for the preparation of a compound of the general formula III as claimed in claim 1 which process comprises carbonylating a said MATRIX having reactive hydroxyl groups in an organic solvent at a temperature of 0° C. to 80° C., the upper temperature limit being the degradation temperature of said MATRIX, with a carbonylating agent of the general formula IV:

$$Y-\underset{\underset{O}{\|}}{C}-Y \qquad IV$$

wherein Y is selected from the group consisting of an imidazolyl, 1,2,3-triazolyl, and 1,2,3-benzotriazolyl.

9. The process of claim 8 wherein said organic solvent is a member selected from the group consisting of dioxan, dimethyl formamide and acetone.

10. The process as claimed in claim 9 wherein said MATRIX is selected from the group consisting of agarose, starch, dextran, cellulose, regenerated cellulose, hydroxy $C_2$–$C_4$ alkylated cellulose and hydroxy $C_2$–$C_4$ alkylated regenerated cellulose substituted by $C_2$–$C_8$ alkyl or alkenyl groups.

11. A process as claimed in claim 10 wherein said MATRIX is cross-linked allyl dextran and Y is imidazolyl.

12. The process as claimed in claim 9 wherein said MATRIX is a copolymer of polyacrylamide with a cross-linked substituted or unsubstituted polysaccharide selected from the group consisting of: agarose, starch, dextran, cellulose, regenerated cellulose, hydroxy $C_2$–$C_4$ alkylated cellulose and hydroxy $C_2$–$C_4$ alkylated regenerated cellulose.

13. The process as claimed in claim 12 where said MATRIX is an agarose/polyacrylamide copolymer and Y is imidazolyl.

14. The process as claimed in claim 9 wherein said MATRIX is a said rigid support comprising silica beads with pendant $$-CH_2CHCH_2O-$$
$$\phantom{-CH_2}|$$
$$\phantom{-CH_2C}OH$$

radicals and Y is imidazolyl.

15. The process as claimed in claim 9 wherein said MATRIX is hydroxyethyl methacrylate and Y is imidazolyl.

* * * * *